(12) United States Patent
Ford et al.

(10) Patent No.: US 9,439,658 B2
(45) Date of Patent: Sep. 13, 2016

(54) DRILL BIT PACKAGE ASSEMBLY

(71) Applicant: SpineDriver, LLC, Marina del Rey, CA (US)

(72) Inventors: Craig Ford, Marina del Rey, CA (US); Robert Jones, Cedar Park, TX (US)

(73) Assignee: SpineDriver, LLC, Marina del Rey, CA (US)

( * ) Notice: Subject to any disclaimer, the term of this patent is extended or adjusted under 35 U.S.C. 154(b) by 221 days.

(21) Appl. No.: 14/120,345

(22) Filed: May 14, 2014

(65) Prior Publication Data

US 2014/0343553 A1 Nov. 20, 2014

Related U.S. Application Data

(60) Provisional application No. 61/823,075, filed on May 14, 2013.

(51) Int. Cl.
| | |
|---|---|
| *B65D 73/00* | (2006.01) |
| *A61B 17/17* | (2006.01) |
| *A61B 17/16* | (2006.01) |
| *A61B 17/00* | (2006.01) |

(52) U.S. Cl.
CPC ....... *A61B 17/1757* (2013.01); *A61B 17/1628* (2013.01); *A61B 50/30* (2016.02); *A61B 50/20* (2016.02); *A61B 2017/0046* (2013.01); *A61B 2017/00734* (2013.01); *A61B 2050/0056* (2016.02); *A61B 2050/3008* (2016.02); *A61B 2050/314* (2016.02); *A61B 2090/034* (2016.02)

(58) Field of Classification Search
CPC ...... B65D 85/27; B65D 77/26; B65D 73/00; B65D 73/0021; A61B 19/0262
USPC .......................... 206/353, 349, 379, 363, 476
See application file for complete search history.

(56) References Cited

U.S. PATENT DOCUMENTS

| | | | |
|---|---|---|---|
| 4,023,678 A | 5/1977 | Fiedler | |
| 4,324,331 A | 4/1982 | Ignasiak | |
| 5,076,431 A | 12/1991 | Thompson | |
| 5,131,542 A | 7/1992 | Stenstrom | |
| 5,226,535 A | 7/1993 | Rosdhy et al. | |
| 5,249,682 A | 10/1993 | Transue | |
| 5,351,822 A * | 10/1994 | Sinn ................. | A61B 17/06138 206/363 |
| 5,375,717 A * | 12/1994 | Roshdy .............. | B65D 73/0021 206/363 |
| 5,699,909 A * | 12/1997 | Foster .................... | A61B 50/30 206/370 |
| 6,691,868 B2 | 2/2004 | Roshdy | |
| 7,055,694 B2 * | 6/2006 | Roshdy .................. | A61B 50/33 206/366 |
| 7,278,852 B2 | 10/2007 | Fischer | |
| 7,328,794 B2 | 2/2008 | Lubs et al. | |
| 8,177,787 B2 | 5/2012 | Walker et al. | |
| 9,072,562 B2 | 7/2015 | Weiner et al. | |
| 2002/0165549 A1 | 11/2002 | Owusu-Akyaw et al. | |
| 2013/0299371 A1* | 11/2013 | Johansson .............. | A61C 19/02 206/349 |
| 2014/0214091 A1 | 7/2014 | Sixto et al. | |
| 2015/0182298 A1 | 7/2015 | Neeman et al. | |
| 2016/0081765 A1 | 3/2016 | Sanders et al. | |

* cited by examiner

*Primary Examiner* — King M Chu
(74) *Attorney, Agent, or Firm* — Kelly & Kelley, LLP

(57) ABSTRACT

A kit system for use in surgery that includes a disposable drill bit, a disposable battery, a reusable adjustable drill guide, and at least one of a battery powered driver and a manual driver that are reusable.

13 Claims, 13 Drawing Sheets

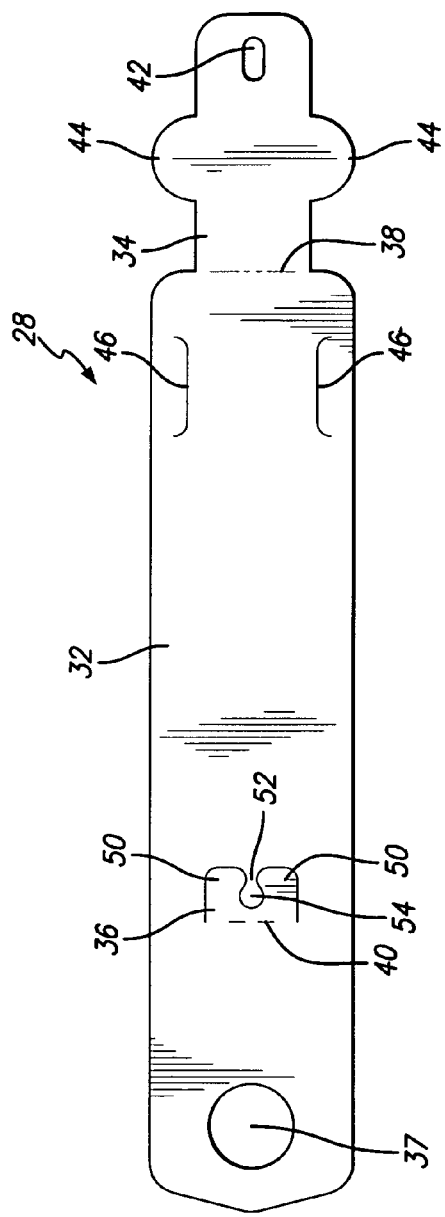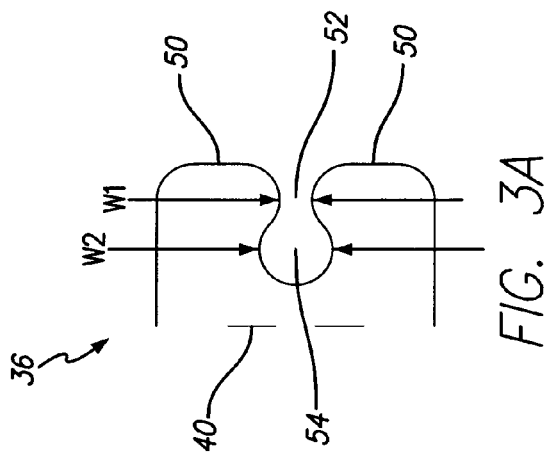
FIG. 3
FIG. 3A

DRILL BIT PACKAGE ASSEMBLY

CROSS REFERENCE TO RELATED APPLICATIONS

This application claims the benefit of U.S. Provisional Application No. 61/823,075 filed May 14, 2013, which is incorporated herein by reference in its entirety.

FIELD OF THE INVENTION

The present invention relates to a kit system for use in spinal surgery, and more particularly to a kit system that includes a reusable bit driver and disposable drill bits.

BACKGROUND OF THE INVENTION

Typically, in Anterior Discectomy and Fusion (ACDF) surgery and other spine related surgeries, manual drivers and drill bits are reused and have to be sterilized with each use.

SUMMARY OF THE PREFERRED EMBODIMENTS

In accordance with a first aspect of the present invention there is provided a kit system for use in surgery that includes a disposable drill bit, a disposable battery, an adjustable drill guide, and at least one of a battery powered driver and a manual driver. In a preferred embodiment, the adjustable drill guide and the battery powered driver and/or the manual driver are included in a first kit and the disposable drill bit and the disposable battery are included in a second kit that is separate from the first kit. Preferably, the second kit includes a plurality of disposable drill bits and a plurality of disposable batteries. In a preferred embodiment, the kit system includes both a battery powered driver and a manual driver.

In a preferred embodiment, the disposable drill bit is secured to a card assembly, and the card assembly and disposable drill bit are disposed in a sterile pouch. Preferably, the disposable drill bit includes a shaft portion and a blade portion, the shaft portion is received in a snap fit portion of the card assembly and the blade portion is received in a bit pocket of the card assembly. In a preferred embodiment, the adjustable drill guide includes an upper tube and a guide tube threadingly engaged with one another and a handle shaft that extends from the upper tube at an angle. The upper tube and the guide tube cooperate to form an internal guide tunnel that is configured to receive at least a portion of the drill bit.

In accordance with another aspect of the present invention there is provided a method that includes the steps of (a) obtaining a first kit that includes a bit driver, (b) obtaining a second kit that includes first and second disposable drill bits, (c) performing a surgery using the first disposable drill bit together with the bit driver, (d) disposing of the first disposable drill bit, and (e) performing a surgery using the second disposable drill bit together with the bit driver. Preferably, the first kit includes an adjustable drill guide, and step (c) includes performing the surgery using the first disposable drill bit together with the bit driver and the adjustable drill guide, and step (e) includes performing the surgery using the second disposable drill bit together with the bit driver and the adjustable drill guide. In a preferred embodiment, the bit driver is a battery powered driver, the second kit includes first and second batteries, step (c) includes performing the surgery using the first disposable drill bit and the first battery together with the battery powered driver and the adjustable drill guide, the method includes the step of disposing of the first battery prior to step (e), and step (e) includes performing the surgery using the second disposable drill bit and the second battery together with the battery powered driver and the adjustable drill guide.

In a preferred embodiment, the first disposable drill bit is secured to a first card assembly, the first card assembly and the first disposable drill bit are disposed in a first sterile pouch, the second disposable drill bit is secured to a second card assembly, and the second card assembly and the second disposable drill bit are disposed in a second sterile pouch.

In accordance with another aspect of the present invention there is provided a card assembly for use with a drill bit. The card assembly includes a main body portion that includes first and second ends and a snap fit portion positioned between the first and second ends. The snap fit portion includes first and second arms that cooperate to define a receiver slot and a bit recess, and the receiver slot is narrower than the bit recess. The card assembly also includes a shield portion connected to the first end of the main body portion along a fold. The shield portion is foldable with respect to the main body portion between a deployed position and a non-deployed position. The shield portion includes a bit opening defined therein, and the shield portion and the main body portion cooperate to define a bit pocket when the shield portion is in the deployed position. Preferably, the snap fit portion is connected to the main body portion along a fold, and the snap fit portion is foldable between a non-deployed position and a deployed position.

In a preferred embodiment, the main body portion includes a finger hole defined therein at a location adjacent the second end thereof. Preferably, the shield portion includes first and second flaps, the main body portion includes first and second slots defined therein, and the first and second flaps are received in the first and second slots when the shield portion is in the deployed position. In a preferred embodiment, the second end of the main body portion has a chevron shape.

In accordance with another aspect of the present invention there is provided a drill bit package assembly that includes a card assembly, a drill bit that includes a shaft portion and a blade portion, and is removably secured to the card assembly, and a sterile pouch that defines an interior. The card assembly and drill bit are disposed in the interior of the sterile pouch. In a preferred embodiment, the card assembly includes a main body portion that includes first and second ends, a snap fit portion positioned between the first and second ends, and a bit pocket adjacent the first end of the main body portion. Preferably, the shaft portion of the drill bit is received in the snap fit portion of the card assembly and the blade portion of the drill bit is received in the bit pocket of the card assembly. Preferably, the snap fit portion includes first and second arms that cooperate to define a receiver slot and a bit recess. The receiver slot is narrower than the bit recess, the receiver slot is narrower than a diameter of the shaft portion, and the bit recess is wider than the diameter of the shaft portion.

In a preferred embodiment, the card assembly includes a shield portion connected to the first end of the main body portion along a fold, and the shield portion is foldable with respect to the main body portion between a deployed position and a non-deployed position. The shield portion includes a bit opening defined therein. The shield portion and the main body portion cooperate to define the bit pocket when the shield portion is in the deployed position, and the drill bit extends through the bit opening such that the blade portion is disposed in the bit pocket.

In accordance with another aspect of the present invention there is provided an adjustable drill guide that includes an upper tube and a guide tube. The upper tube includes a main body portion, external threads disposed on the main body portion, and a collet extending from a distal end of the main body portion. An upper tube tunnel extends axially through the upper tube, and at least a portion of the upper tube tunnel includes internal threads. The guide tube has a proximal end and a distal end and includes a guide tube tunnel extending therethrough. The guide tube includes external threads on a proximal end thereof that are matingly engaged with the internal threads of the upper tube. The upper tube tunnel and the guide tube tunnel cooperate to define an internal guide tunnel extending therethrough that is configured to receive a drill bit.

In a preferred embodiment, the adjustable drill guide includes a handle shaft that extends from the upper tube at an angle between about 10° and about 90°. Preferably, the main body portion includes a window defined therein and includes measurement indicia disposed adjacent the window. The proximal end of the guide tube is visible through the window. In a preferred embodiment, the adjustable drill guide includes a barrel having a barrel tunnel extending axially therethrough and that includes internal threads that are matingly received on the external threads of the upper tube. The guide tube extends through the barrel tunnel and the collet.

Generally, the present invention includes single-use, pre-packaged sterile, disposable drill bits to be used during Anterior Discectomy and Fusion (ACDF) surgery, and other spine related surgeries, small bone surgeries, and craniomaxillofacial surgeries in conjunction with a battery powered reusable driver.

In accordance with an aspect of the present invention, there is provided a kit for use in spinal surgery. The kit preferably includes a battery powered bit driver (drill), a manual bit driver, a disposable bit, an adjustable drill guide to facilitate linear drilling and depth control as the bit is drilled through or into bone or through any plating system (e.g., a cervical plate) to form a screw hole, and a disposable battery. In a preferred embodiment, the kit includes a sterilizable tray. Preferably, the proximal end of the bit and the collet of the driver uniquely mate with each other. Preferably, the powered bit driver is configured such that it is in-line and the battery is snap fitted to the distal end of the driver to provide for ready replacement.

In accordance with another aspect of the present invention, there is provided a system for facilitating ACDF surgery that includes providing an in-line battery powered driver to a user of the driver; and providing a pack of more than one individually wrapped, pre-sterilized and disposable drill bits and/or batteries to the user. A new drill bit and/or new battery is used in conjunction with the driver during each surgery. Preferably, each disposable drill bit is packaged individually within sterile packaging. Preferably, each disposable battery is also packaged individually within sterile packaging. In a preferred embodiment, the sterile packaging includes a plastic card (holder) that secures the bit in place. The card has a shield portion or flap that protects the sharp edge of the bit from coming into contact with the outer pouch. That bit card fits into a pouch and is sealed for sterilization. In a preferred embodiment, the pouch is made of Tyvek®. However, this is not a limitation on the present invention, and the pouch can be made of other materials.

The invention, together with additional features and advantages thereof, may be best understood by reference to the following description.

BRIEF DESCRIPTION OF THE DRAWINGS

FIG. 3 is a plan view of a card assembly in accordance with a preferred embodiment of the present invention;

FIG. 3A is close up of the snap fit portion of the card assembly of FIG. 3;

Like numerals refer to like parts throughout the several views of the drawings.

DETAILED DESCRIPTION OF THE PREFERRED EMBODIMENTS

Figure 1:
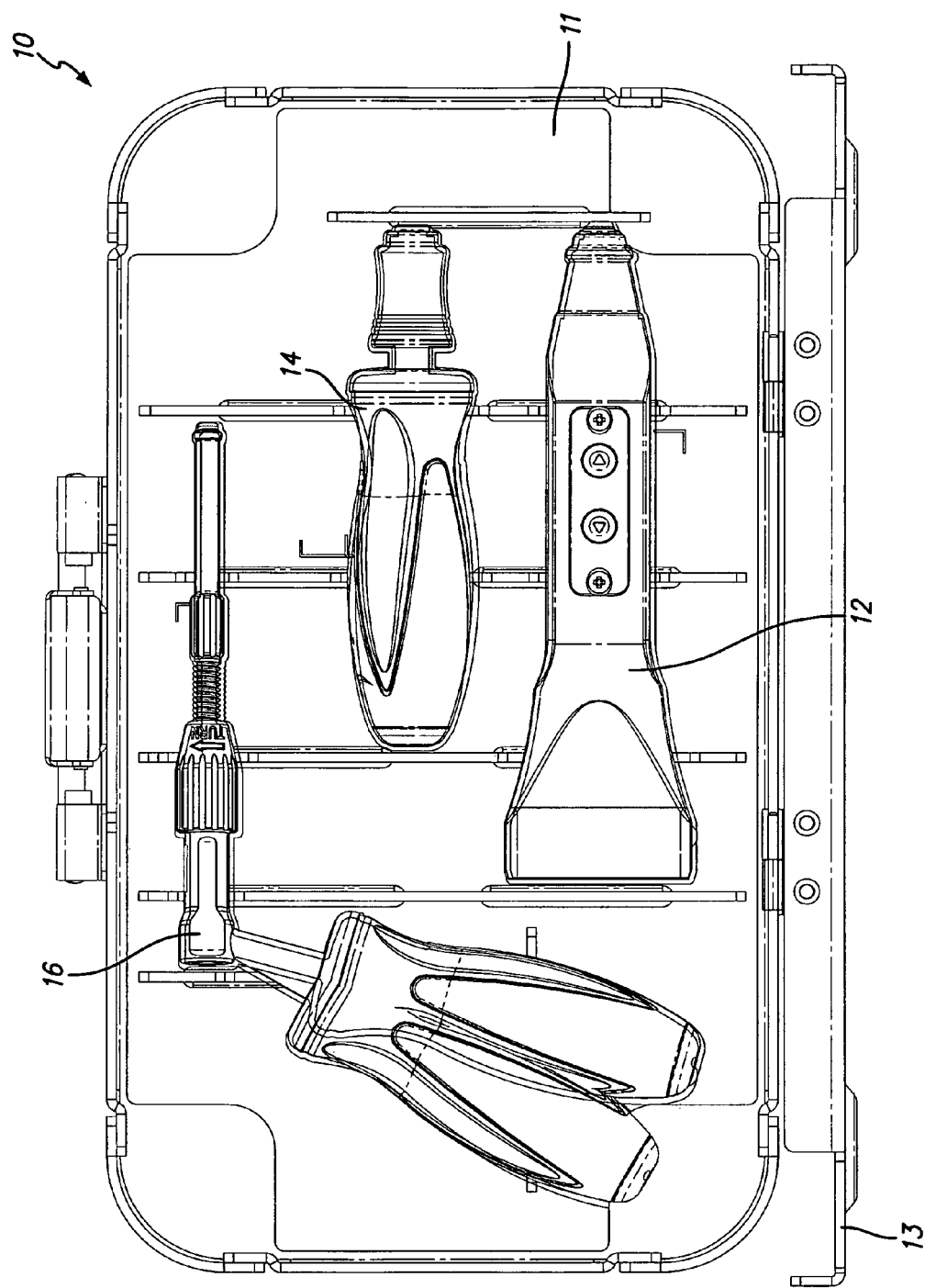
FIG. 1 is a plan view of a first kit that includes an adjustable drill guide (showing two different angled handles), a manual driver and a battery powered driver in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an other embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

Figure 2:
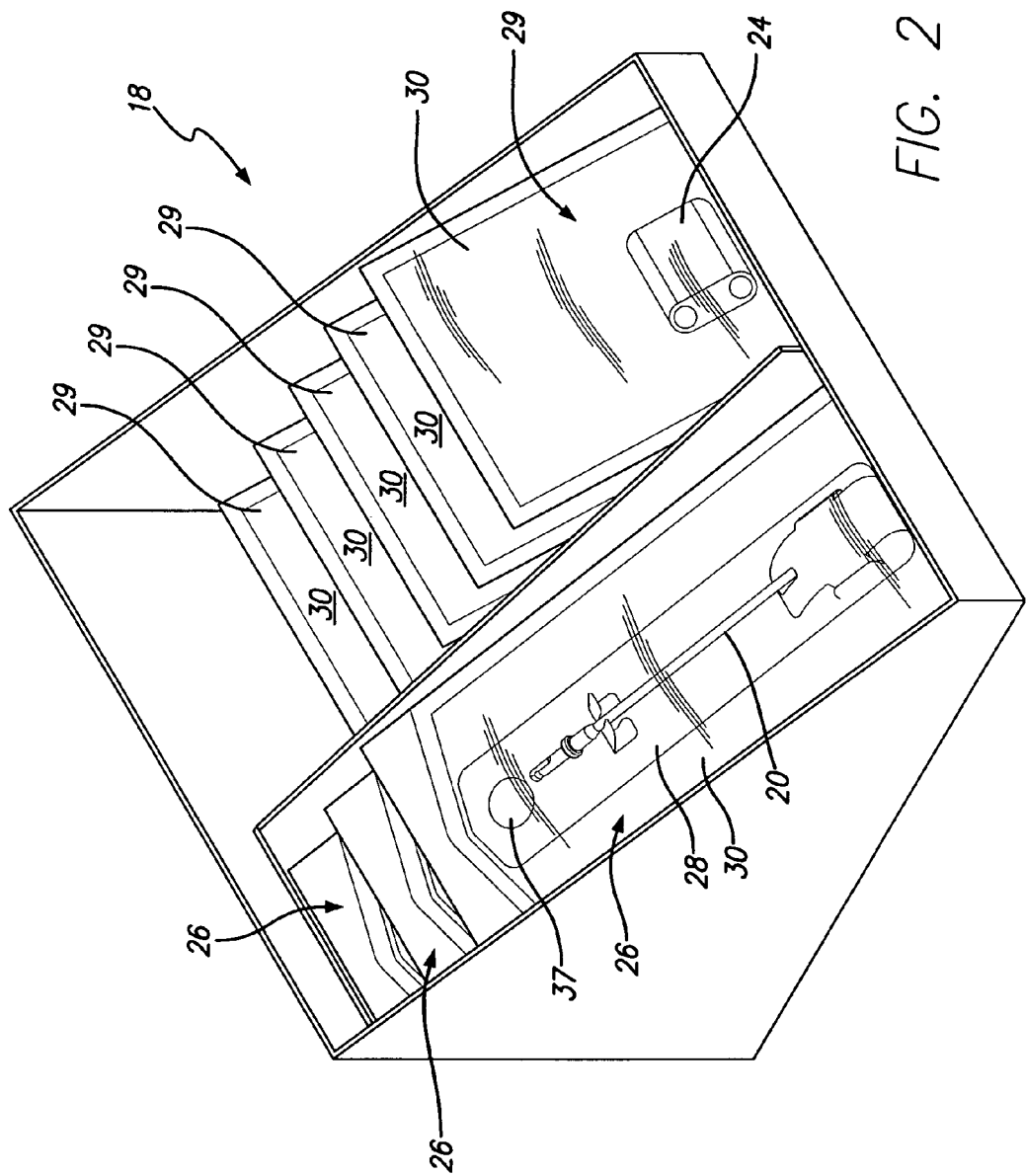
FIG. 2 is a perspective view of a second kit that includes a plurality of sterile drill bit package assemblies and a plurality of sterile battery packages for use with the first kit of FIG. 1.

Referring now to the drawings, wherein the showings are for purposes of illustrating the present invention and not for purposes of limiting the same, FIGS. 1-14 show a spine driver system. FIG. 1 shows a first kit 10 that generally includes a tray or container 11 having a lid 13 and that includes a battery powered driver 12, manual driver 14, and an adjustable drill guide 16 (for bit depth control). FIG. 2 shows a second kit 18 with a box or container 19 that includes a plurality of sterile, disposable drill bits 20 (provided in a drill bit package assembly 26 that includes a sterile pouch 30) and a plurality of sterile, disposable batteries 24 (provided in a battery package 29 that includes a sterile pouch 30).

As discussed above, generally, the present invention includes single-use, pre-packaged sterile, disposable drill bits 20 to be used during Anterior Discectomy and Fusion (ACDF) surgery and other spine related surgeries in conjunction with the battery-powered reusable driver 12. In use, the hospital, surgery center or surgeon who ultimately performs the surgery is provided with the first kit 10, which is reusable. The surgeon is then provided with the second kit 18, which includes the disposable drill bit package assemblies 26 and battery packages 29, respectively. In another embodiment, the disposable drill bit package assemblies 26 and battery packages 29 can be provided in separate boxes or in any other type of container, bag, etc. The inclusion of a box is not limiting. For each surgery performed, the components of the first kit 10 can be reused, while a new disposable drill bit 20 and battery 24 are used. The system generally includes a reusable first kit 10 (and the components thereof) and the single use drill bits 20 and batteries 24. In another embodiment, the batteries 24 can be omitted and the second kit 18 only includes the drill bits 20 or disposable drill bit package assemblies 26.

In a preferred embodiment, the tray 11 and components thereof are sterilizable. However, this is not a limitation on the present invention. It will be appreciated by those of ordinary skill in the art that the manual driver 14 is included for surgeons who do not wish to use the battery powered driver 12 or in situations where the battery powered driver 12 is otherwise not usable. In another embodiment, the manual driver 14 can be omitted from the first kit 10. In yet another embodiment, the battery powered driver 12 can be omitted from the first kit 10. Any type of bit driver is within the scope of the present invention.

It is contemplated that the first kit 10 can be provided for free as a loaner or on consignment to the user, and the disposable drill bits 20 and batteries 24 can be sold to the user as needed. The user can continue to keep the first kit 10 provided they stock the disposable bits 20 and batteries 24 and maintain them at a predetermined volume.

For the initial use, the first kit 10 can include a disposable drill bit 20 and/or a disposable battery 24. However, it will be understood, that the disposable drill bit 20 and disposable battery 24 are disposed after the initial surgery, wherein the powered driver 12, manual driver 14 and adjustable drill guide 16 can be reused as desired.

In a preferred embodiment, the driver 14 and drill bit 20 are in-line or co-axial. However, this is not a limitation on the present invention and the driver 14 and drill bit 20 can include an offset.

Figure 4:
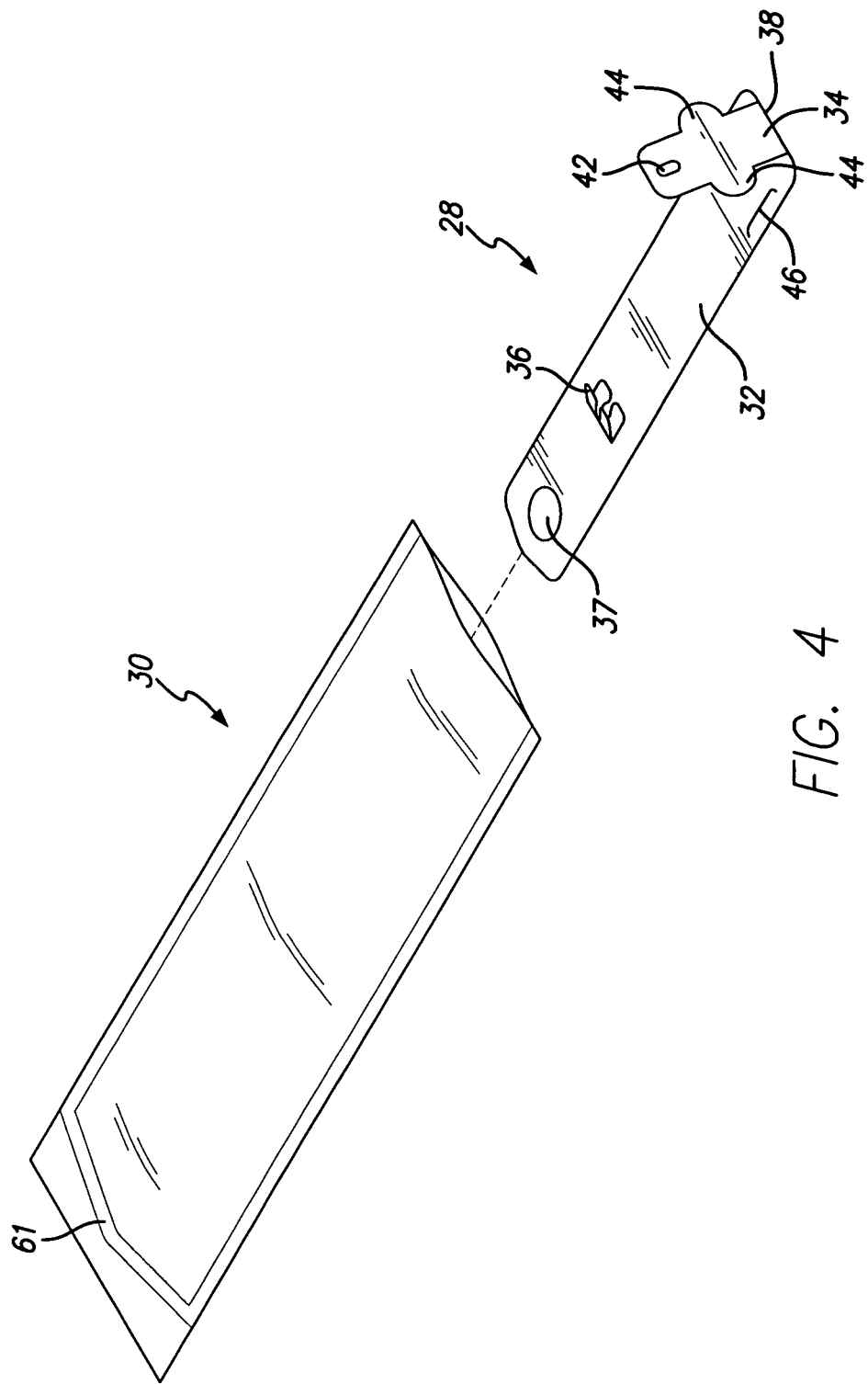
FIG. 4 is an exploded view of a card assembly and pouch in accordance with a preferred embodiment of the present invention.
Figure 5:
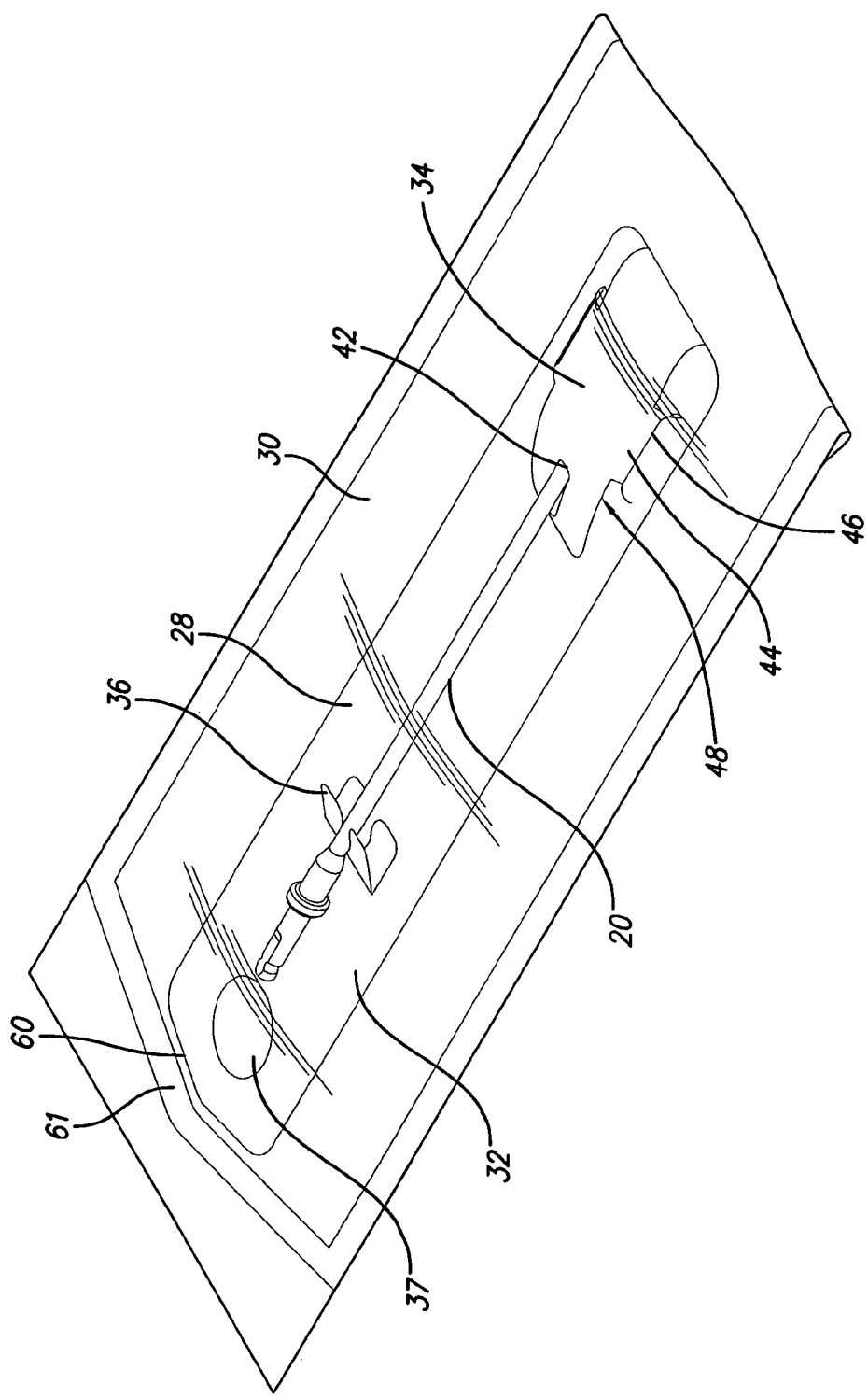
FIG. 5 is a perspective view of the drill bit package assembly.
Figure 6:
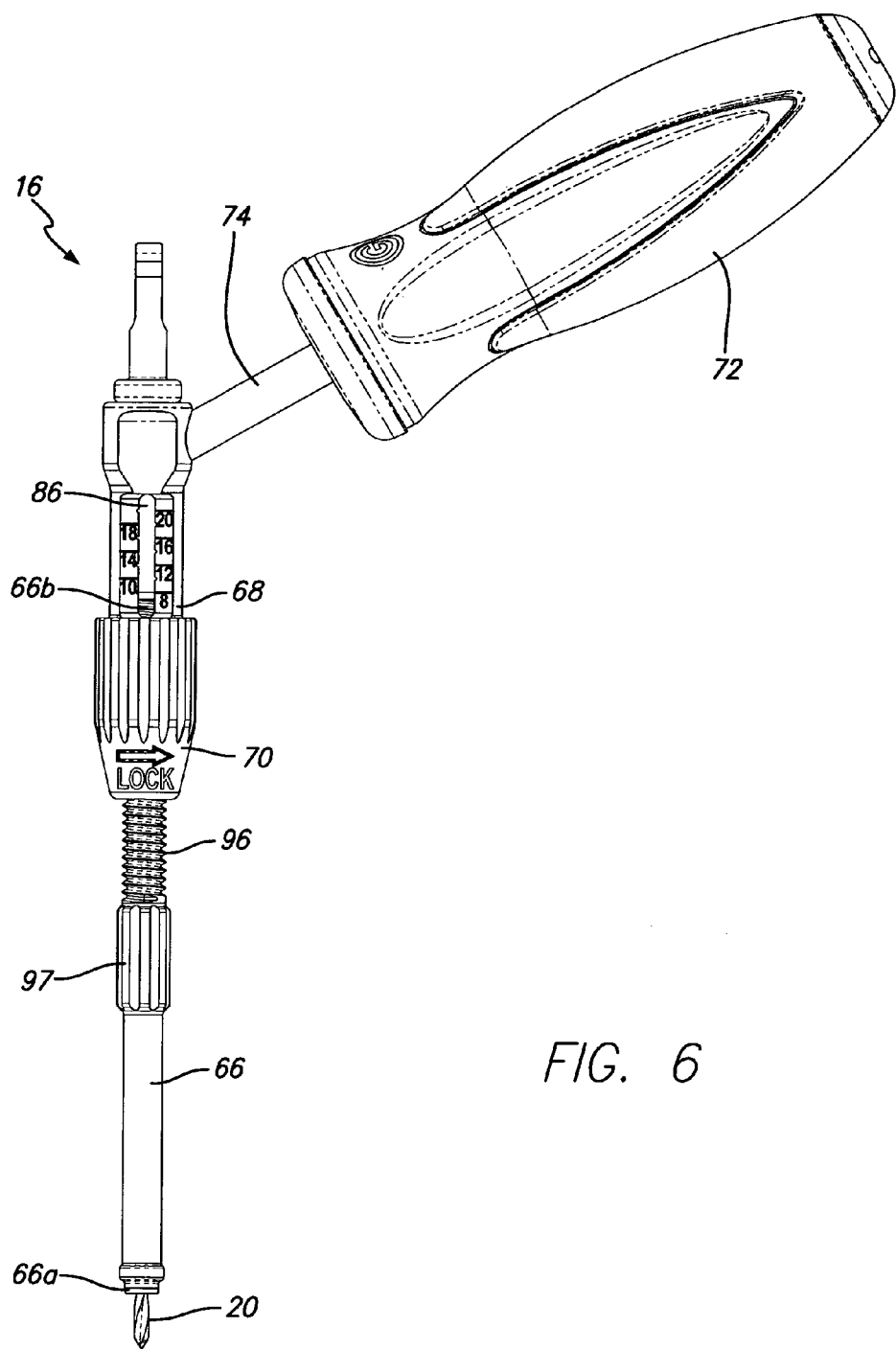
FIG. 6 is an elevational view of an adjustable drill guide together with a drill bit in accordance with a preferred embodiment of the present invention.

As is best shown in FIGS. 3-5, in a preferred embodiment, the drill bits 20 are provided in the drill bit package assembly 26 that includes a "snap-fit" bit card assembly 28 that is received in a pouch 30. The card assembly 28 is preferably made of plastic or the like. As shown in FIG. 3, the card assembly 28 includes a main body portion 32 and a shield portion 34. The main body portion 32 includes a snap fit portion 36 and a finger hole 37 defined therethrough. Prior to the drill bit 20 being placed on the card assembly 28, the card assembly 28 is in a flat configuration (FIG. 3).

In a preferred embodiment, the shield portion 34 is foldable with respect to the main body portion 32 along a first fold 38 and the snap fit portion 36 is foldable with respect to the main body portion 32 along a second fold 40. The shield portion 34 is movable along the first fold 38 between a non-deployed position (FIG. 3) and a deployed position (FIG. 5). FIG. 4 shows the shield portion partially folded. In a preferred embodiment, the shield portion 34 includes a bit opening 42 defined therein and a pair of flaps 44 that are received in slots 46 defined in the main body portion, when the shield portion 34 is in the deployed position. As shown in FIG. 5, in the deployed position, the shield portion 34 and the main body portion 32 cooperate to define a bit pocket 48.

In use, a portion of the drill bit 20 extends through the bit opening 42 and a blade portion 104 of the drill bit 20 is received in the bit pocket 48.

Snap fit portion 36 is foldable along the second fold 40 and includes first and second arms 50 that cooperate to define a receiver slot 52 and a bit recess 54. As shown in FIG. 3A, in a preferred embodiment, the receiver slot 52 defines a first width W1 and the bit recess 54 defines a second width W2. The first width W1 is narrower than the second width W2. Therefore, the receiver slot 52 is narrower than the bit recess 54. It will be understood that the first width W1 is narrower than the diameter of a drill bit 20 (e.g., a shaft portion 102 of the drill bit 20) and the second width W2 is wider than the diameter of the shaft portion 102 of the drill bit 20. This allows the drill bit to snap fit through the receiver slot 52 and be retained in the bit recess 54.

To assemble the card assembly 28 together with a drill bit 20, the shield portion 34 is folded with respect to the main body portion 32 along first fold 38 and the flaps 44 are inserted through the slots 46 to form pocket 48. The working or distal end 20a of a drill bit 20 is then inserted through bit opening 42 such that the distal end 20a is received in pocket 48. The snap fit portion 36 is then folded with respect to the main body portion 32 along the second fold 40. Next, the drill bit 20 is then snap fit through the receiver slot 52 and into the bit recess 54. To form the drill bit package assembly 26, the card assembly 28 and drill bit 20 are then placed in the pouch 30 and the pouch 30 is sealed.

The pouch 30 includes a closed end 56 and an open end 58. In a preferred embodiment, when the card assembly 28 is received in the pouch 30, the finger hole 37 is positioned adjacent the open end 58. Therefore, in use, after the pouch 30 is unsealed, a user can place their finger through the finger hole 37 to remove the card assembly 28 and bit 20. In a preferred embodiment, the batteries 24 are also disposed within a sterile pouch 30 or other packaging. As shown in FIG. 5, in a preferred embodiment, the end of the card assembly 28 opposite the shield portion 34 has a chevron shape 60 that is received in a similarly shaped portion 61 of the pouch 30 that is adjacent the open end 58.

FIGS. 6-10 show a preferred embodiment of the adjustable drill guide 16. Preferably, the adjustable drill guide 16 generally includes a guide tube 66, an upper tube 68, a barrel 70, a handle 72 and a handle shaft 74. In a preferred embodiment, the handle shaft 74 is attached to the upper tube 68 and extends at an angle therefrom. The angle allows a drill bit 20 to be inserted into the proximal opening 75 in the upper tube 68. Different adjustable drill guides 16 can be provided with different angled handle shafts 74, e.g., 60° and 75°. Different angles can be used for different patient anatomies and different surgeries. Any angle between about 10° and about 90° is within the scope of the present invention. FIG. 1 shows two different angled handle shafts 74 and handles 72 in the first kit 10. The handle 72 can be temporarily (e.g., by threads 77) or permanently attached to the handle shaft 74.

Figure 7:
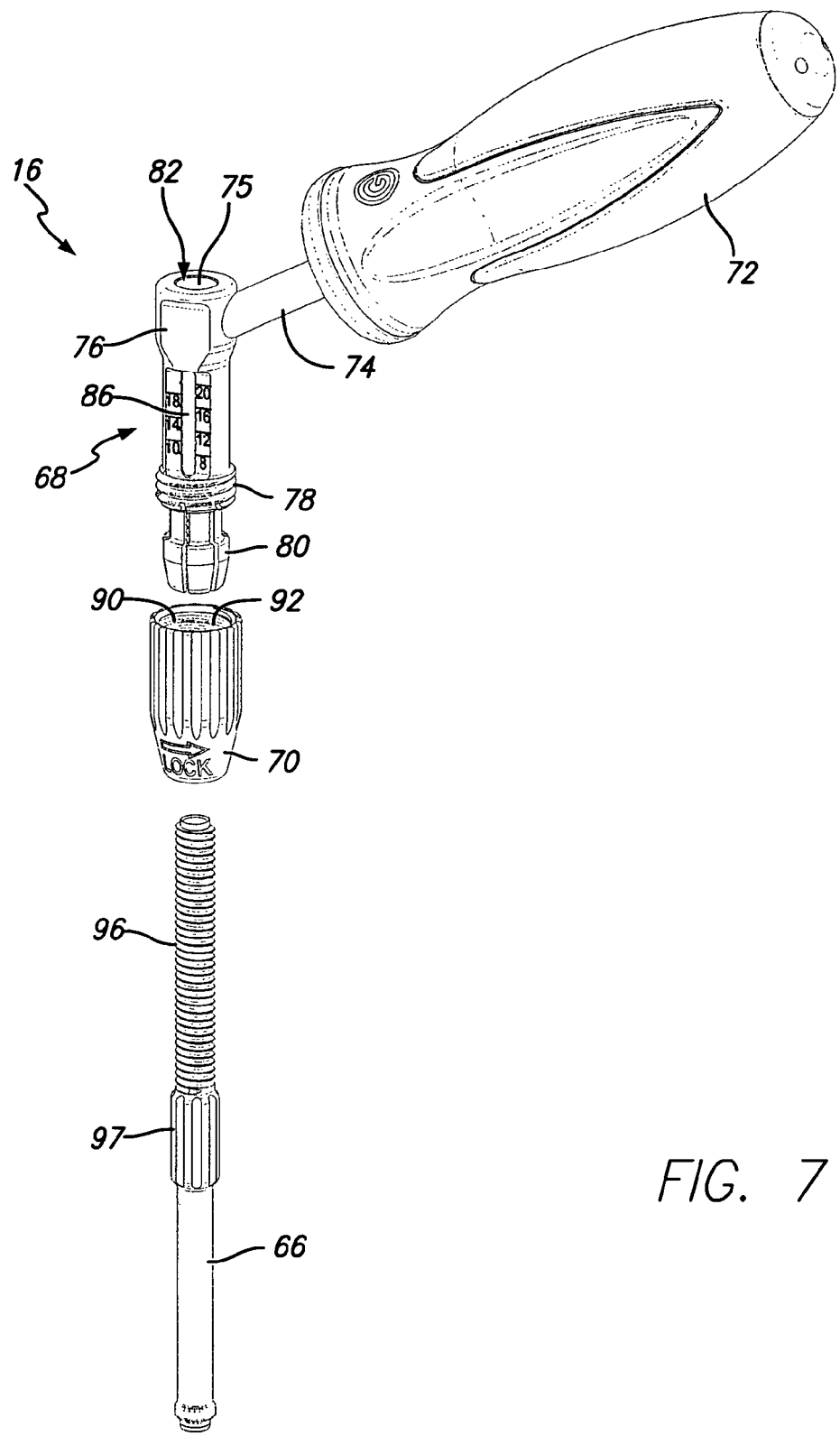
FIG. 7 is an exploded view of the adjustable drill guide of FIG. 6.
Figure 8:
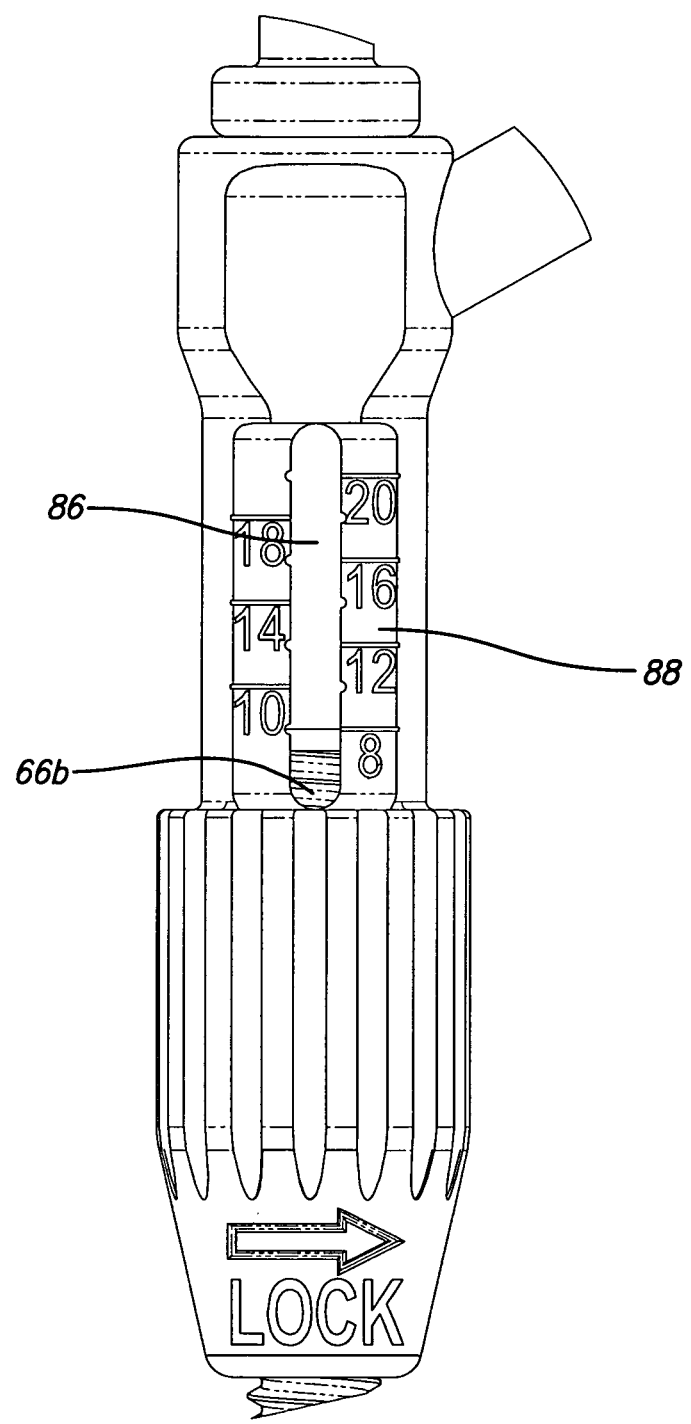
FIG. 8 is a close up of the upper tube and barrel of the adjustable drill guide of FIG. 6 showing the window and measurement indicia.
Figure 9:
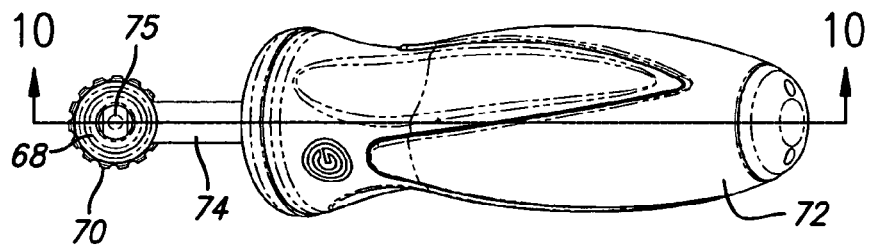
FIG. 9 is a top plan view of the adjustable drill guide of FIG. 6.

As shown in FIG. 7, the upper tube 68 includes a main body portion 76, external threads 78 disposed on the main body portion 76 and a collet 80 extending from a distal end of the main body portion 76. The upper tube 68 also includes an upper tube tunnel 82 extending axially therethrough. The upper tube 68 also includes internal threads 84 and a window 86 defined therein that communicates the upper tube tunnel 82 with the exterior of the upper tube 68 and allows the guide tube 66 to be viewed, as described more fully below. In a preferred embodiment, the main body portion 76 also includes measurement indicia 88 disposed thereon adjacent to the window 86, as is best shown in FIG. 8.

Figure 10:
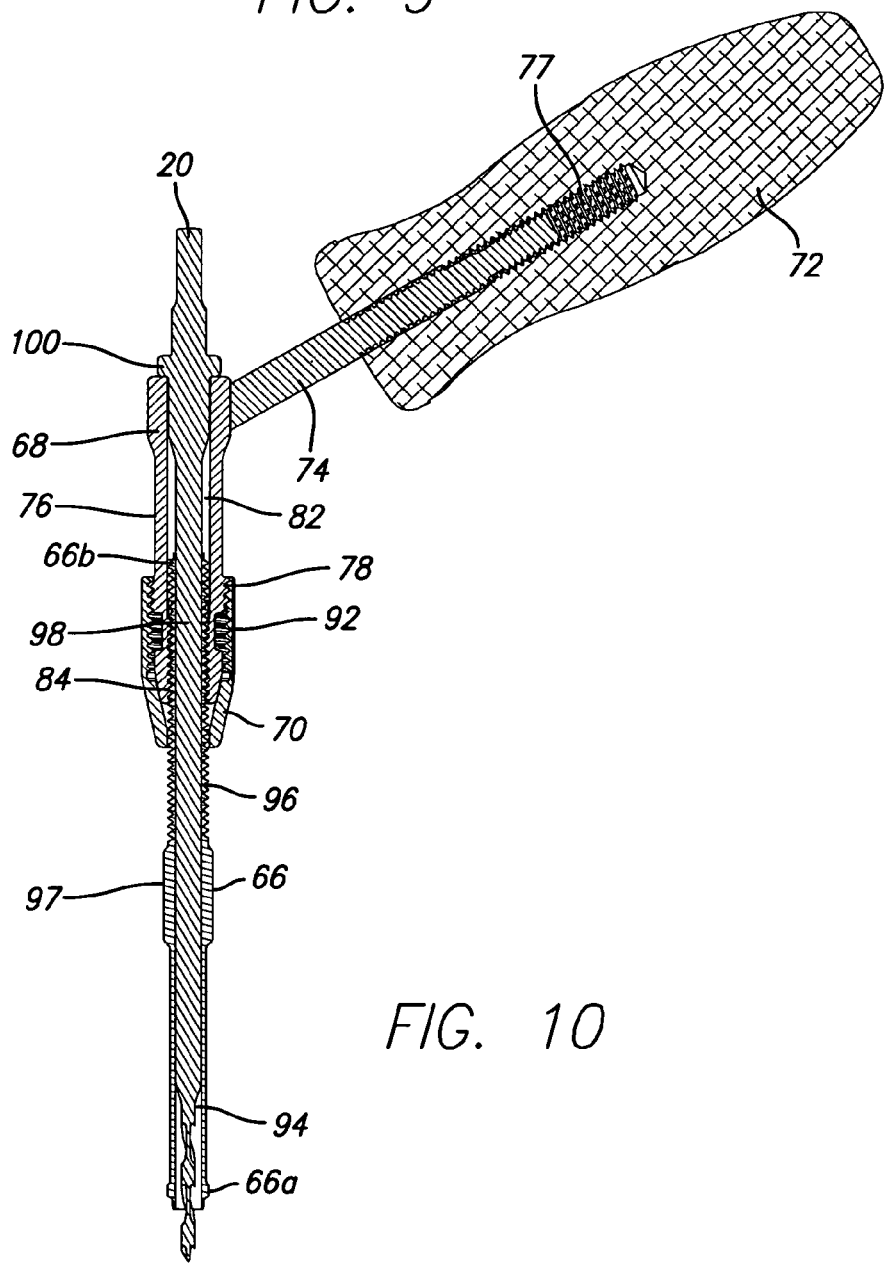
FIG. 10 is a cross section taken along line 10-10 of FIG. 9.

In a preferred embodiment, the barrel 70 includes a barrel tunnel 90 extending axially therethrough and internal threads 92 that are matingly received on the external threads 78 of the upper tube 68. The guide tube 66 includes a guide tube tunnel 94 extending therethrough and external threads 96 on a proximal end thereof that are matingly engaged with the internal threads 84 of the upper tube 68. The guide tube extends through the barrel tunnel 90. As shown in FIG. 10, the upper tube tunnel 82 and the guide tube tunnel 94 cooperate to define an internal guide tunnel 98 extending therethrough that is configured to receive a drill bit 20. The guide tube 66 can include knurls 97 to help with adjustment. However, the knurls can be omitted.

In a preferred embodiment, the drill bits 20 include a collar 100 thereon, that has a wider dimension (e.g., diameter) than the internal guide tunnel 98. This prevents the drill bit 20 from extending too far into the internal guide tunnel 98 and provides repeatability.

In use, the guide tube 66 (which has distal 66a and proximal 66b ends) is axially movable as a result of the interaction of external threads 96 and internal threads 84. As shown in FIG. 8, the proximal end 66b of guide tube 66 is viewable through window 86. The indicia 88 next to the window 86 represent various depths that drill bit 20 will drill to if the proximal end 66b of the guide tube 66 is lined up with the appropriate indicia 88 (e.g., just below the "8" as shown in FIG. 8). In an exemplary embodiment, the 8, 10, 12, 14, 16, 18 and 20 represent 8, 10, 12, 14, 16, 18 and 20 millimeter deep holes that will be drilled. In other words, when a drill bit 20 extends through the internal guide tunnel 98, as shown in FIG. 8, if the proximal end 66b of the guide tube 66 is lined up just below the "8", the distal end 20a of the drill bit extends just under eight millimeters outside the distal end 66a of the guide tube 66 (see FIG. 10). Therefore, a hole with a depth of just under eight millimeters will be drilled.

It will be appreciated by those of ordinary skill in the art that the barrel 70 can be rotated to secure or lock the guide tube 66 in place. When the barrel 70 is rotated clockwise (due to right handed threads) the barrel 70 squeezes the collet 80 which then squeezes the guide tube 66 to lock it in place and prevent axial movement via rotation. To adjust the axial position of the guide tube 66 (and the depth of a resulting hole), the barrel 70 is loosened, the guide tube 66 is rotated and adjusted axially and the guide tube 66 is retightened. This can be done when the drill bit 20 is extending through the internal guide tunnel 98 or when the internal guide tunnel 98 is vacant.

Figure 11:
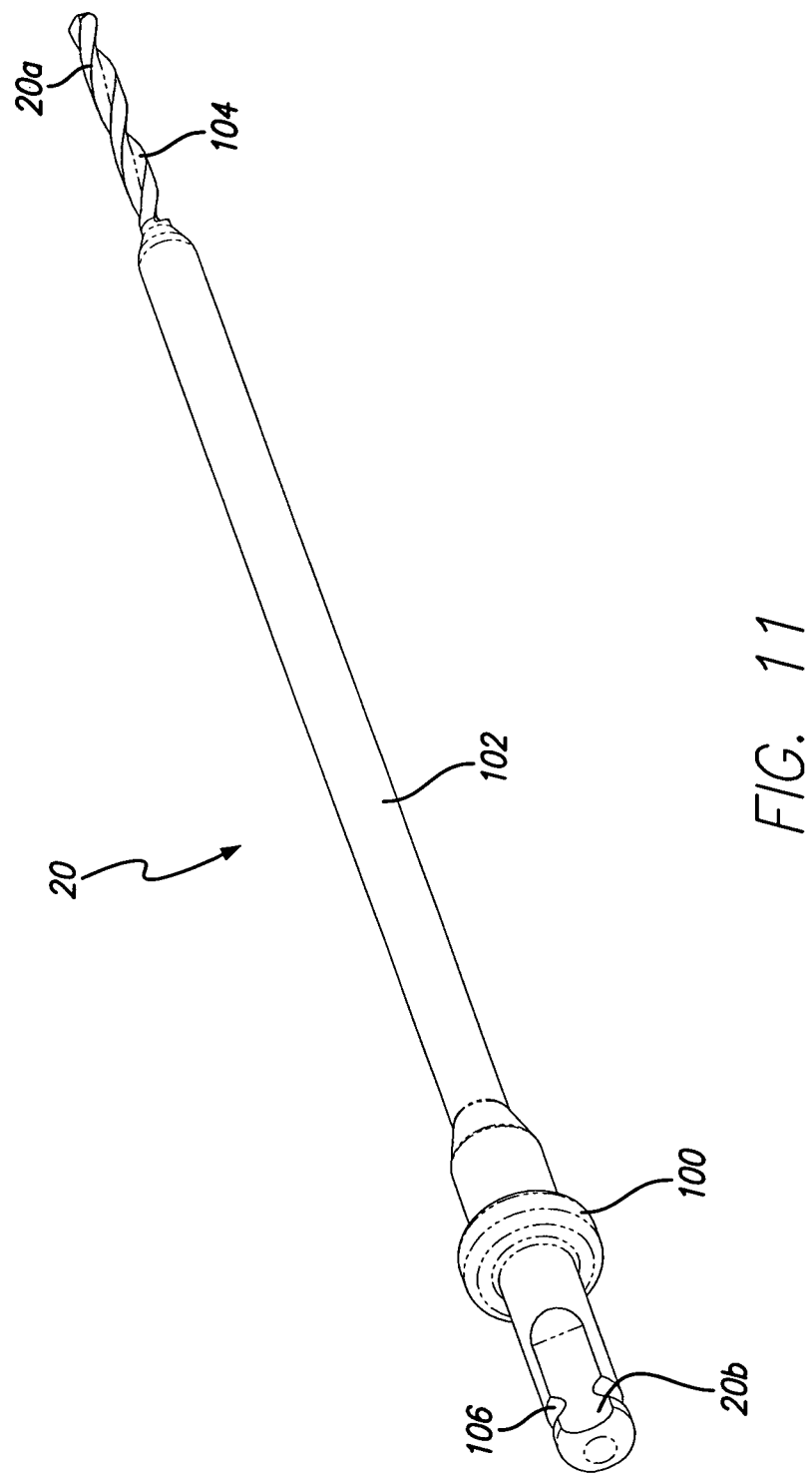
FIG. 11 is a perspective view of a drill bit in accordance with a preferred embodiment of the present invention.
Figure 12:
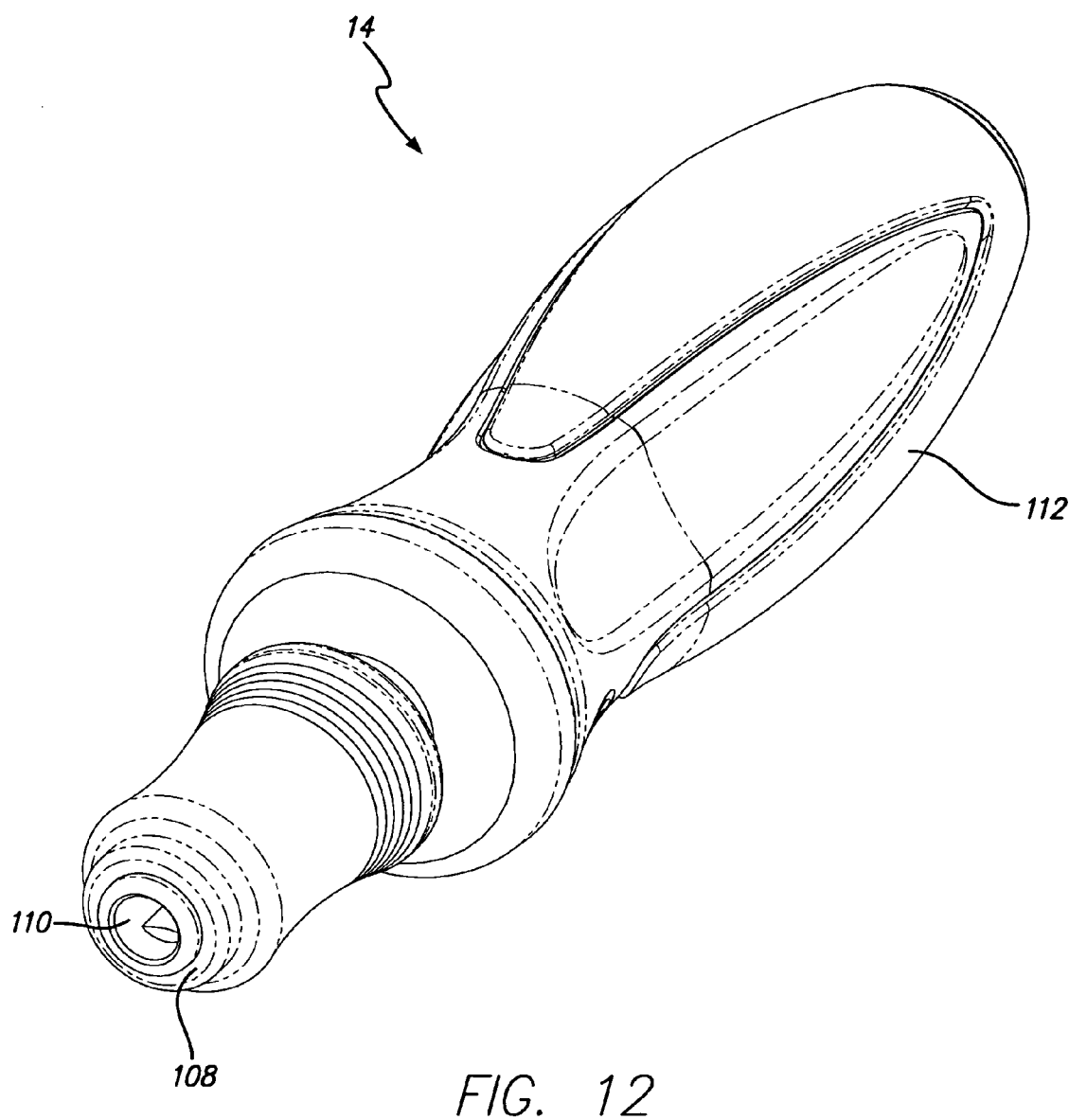
FIG. 12 is a perspective view of a manual driver in accordance with a preferred embodiment of the present invention.
Figure 13:
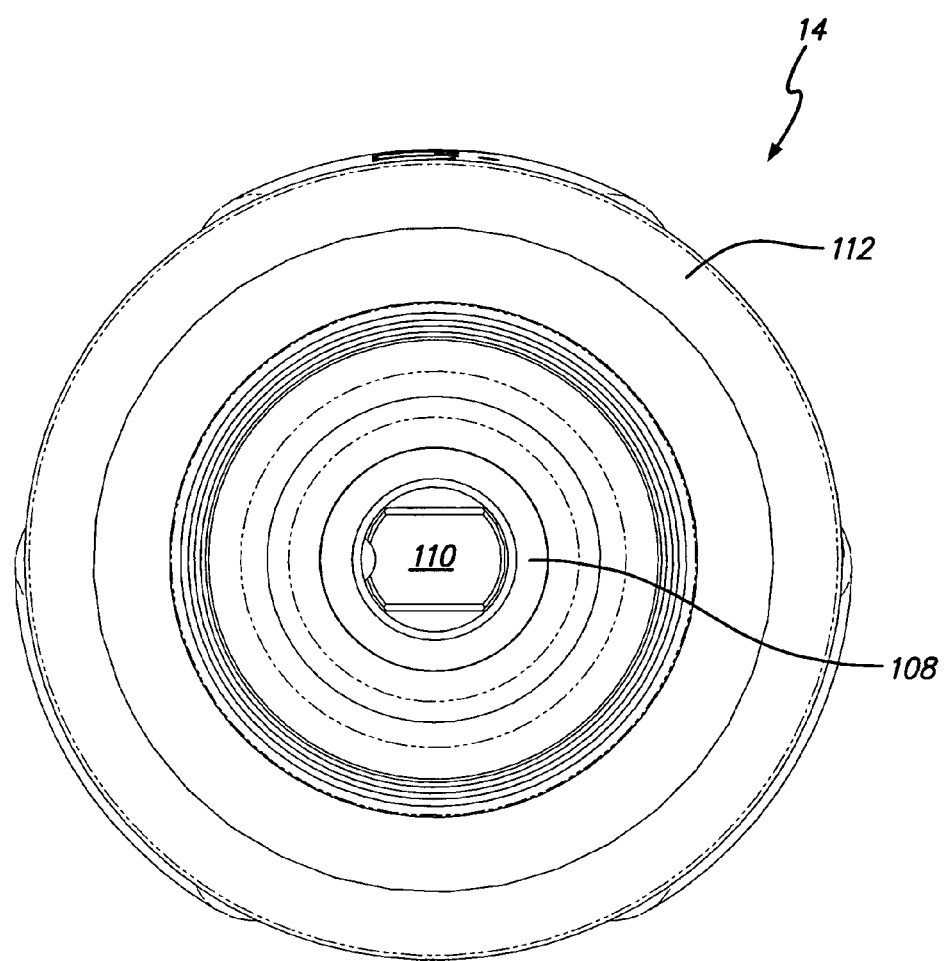
FIG. 13 is an end view of the manual driver of FIG. 12.

As shown in FIG. 11, the drill bit 20 includes collar 100, a shaft portion 102, a blade portion 104 at the distal end 20a and a proximal end 20b that includes a modified ao fitting 106 so that it can only mate with a collet 108 and opening 110 on the battery powered driver 12 and the manual driver 14 (shown in FIGS. 12-13). The collet 108 and opening 110 of the manual driver 14 is shown in FIG. 13. The battery powered driver 12 includes the same collet 108 and opening 110. It will be appreciated that the opening 110 is uniquely shaped to mate with the proximal end 20b of the drill bit 20. In other words, the bit 20 and collet 108/opening 110 are designed so they only fit with one another. Any type of fitting that accomplishes this is within the scope of the present invention.

Figure 14:
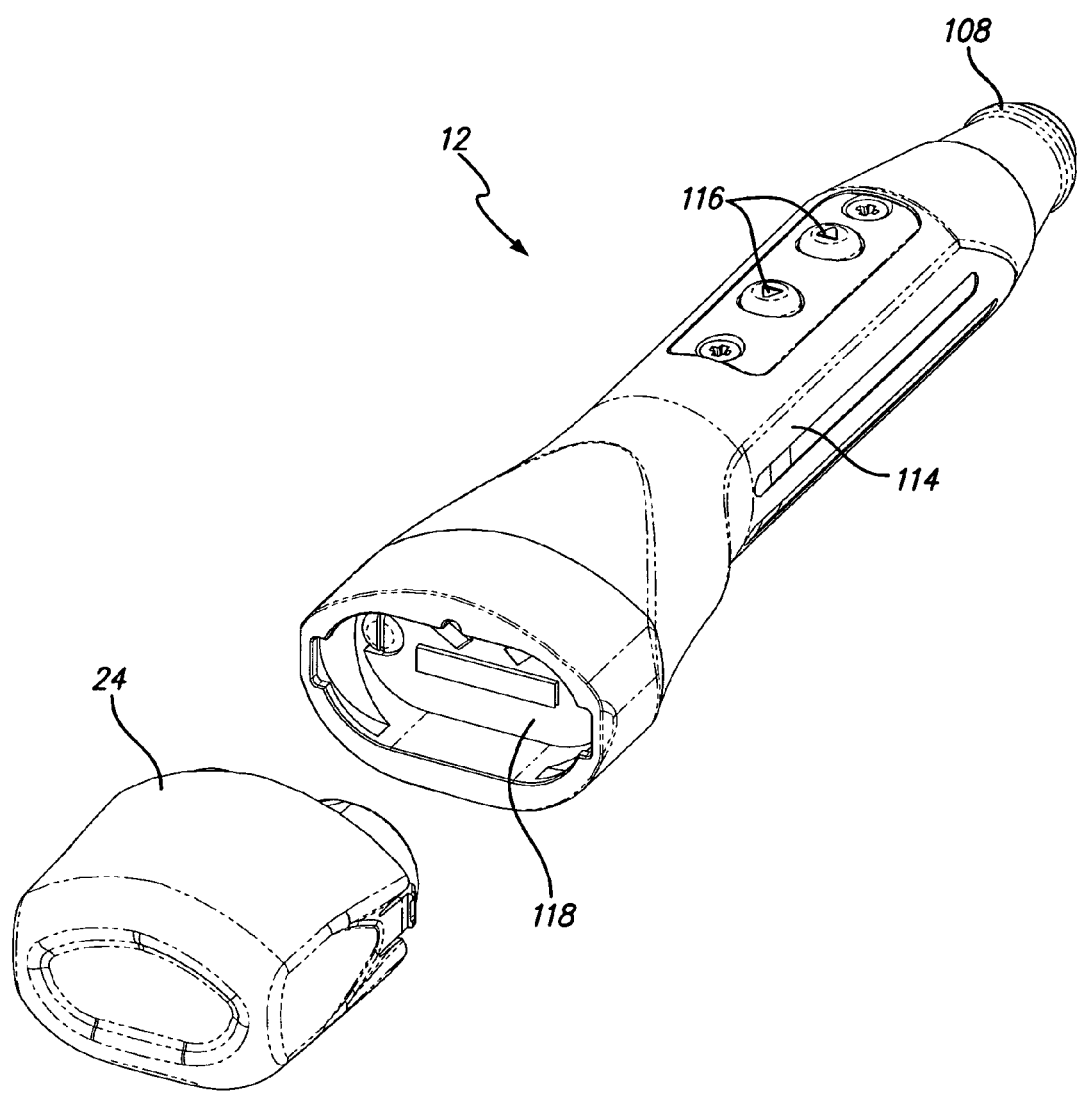
FIG. 14 is a perspective view of a battery powered driver and battery exploded therefrom in accordance with a preferred embodiment of the present invention.

As shown in FIG. 12, the manual driver 14 includes collet 108 and a handle 112 connected thereto. As shown in FIG. 14, the battery powered driver 12 includes collet 108 and a handle portion 114 with control buttons 116 thereon (e.g., forward and reverse). Internally, the battery powered driver 12 includes a motor and associated electronics and components to rotate the drill bit 20 as necessary. The battery powered driver 12 also includes a docking portion 118 for docking one of the disposable batteries 24 discussed previously. Therefore, for each separate use, the battery 24 can be replaced.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A card assembly for use with a drill bit, the card assembly comprising:
   a main body portion that includes first and second ends and a snap fit portion positioned between the first and second ends, wherein the snap fit portion includes first and second arms that cooperate to define a receiver slot and a bit recess, wherein the receiver slot is narrower than the bit recess;
   a shield portion connected to the first end of the main body portion along a fold, wherein the shield portion is foldable with respect to the main body portion between a deployed position and a non-deployed position, wherein the shield portion includes a bit opening defined therein, and wherein the shield portion and the main body portion cooperate to define a bit pocket when the shield portion is in the deployed position;
   wherein the snap fit portion is connected to the main body portion along a fold, and wherein the snap fit portion is foldable between a non-deployed position and a deployed position; body portion includes a finger hole defined therein at a location adjacent the second end thereof; and
   wherein the shield portion includes first and second flaps, wherein the main body portion includes first and second slots defined therein, and wherein the first and second flaps are received in the first and second slots when the shield portion is in the deployed portion.

2. The card assembly of claim 1 wherein the second end of the main body portion has a chevron shape.

3. A drill bit package assembly comprising:
   a card assembly comprised of a main body portion that includes first and second ends and a snap fit portion positioned between the first and second ends, and a shield portion connected to the first end of the main body portion along a fold wherein the shield portion is foldable with respect to the main body portion between a deployed position and a non-deployed position, wherein the shield portion includes a bit opening defined therein, and wherein the shield portion and the main body portion cooperate to define a bit pocket when the shield portion is in the deployed position, wherein the shield portion includes first and second flaps, wherein the main body portion includes first and second slots defined therein, and wherein the first and second flaps are received in the first and second slots when the shield portion is in the deployed position,
a drill bit that includes a shaft portion and a blade portion, wherein the drill bit is removably secured to the card assembly, and
a sterile pouch that defines an interior, wherein the card assembly and drill bit are disposed in the interior of the sterile pouch.

4. The drill bit package assembly of claim 3 wherein the shaft portion of the drill bit is received in the snap fit portion of the card assembly and the blade portion of the drill bit is received in the bit pocket of the card assembly.

5. The drill bit package assembly of claim 3 wherein the snap fit portion includes first and second arms that cooperate to define a receiver slot and a bit recess, wherein the receiver slot is narrower than the bit recess, wherein the receiver slot is narrower than a diameter of the shaft portion, and wherein the bit recess is wider than the diameter of the shaft portion.

6. The drill bit package assembly of claim 3 wherein the drill bit extends through the bit opening such that the blade portion is disposed in the bit pocket.

7. The drill bit package assembly of claim 3 wherein the card assembly includes a finger hole through the main body portion and disposed adjacent to the second end thereof so as to be positioned beyond an adjacent shaft portion of the drill bit when held within the card assembly.

8. The drill bit package of claim 3 wherein the snap fit portion includes first and second arms that cooperate to define a receiver slot and a bit recess, wherein the receiver slot is narrower than the bit recess.

9. A drill bit package assembly comprising:
a card assembly comprised of a main body portion that includes first and second ends and a snap fit portion positioned between the first and second ends, wherein the snap fit portion includes first and second arms that cooperate to define a receiver slot and a bit recess, and
a shield portion connected to the first end of the main body portion along a fold, wherein the shield portion is foldable with respect to the main body portion between a deployed position and a non-deployed position, wherein the shield portion includes a bit opening defined therein, and wherein the shield portion and the main body portion cooperate to define a bit pocket when the shield portion is in the deployed position;
a drill bit having a shaft portion and a blade portion, the drill bit being removably secured to the card assembly such that the shaft portion is received in the bit recess of the snap fit portion and the blade portion is received in the bit pocket of the card assembly;
a sterile pouch having an interior in which the card assembly and drill bit are disposed; and
a finger hole through the main body portion of the card assembly and disposed adjacent to the second end thereof so as to be positioned beyond an adjacent shaft portion of the drill bit when held within the card assembly.

10. The drill bit package assembly of claim 9 wherein the sterile pouch includes a chevron-shaped openable seal.

11. The drill bit package assembly of claim 10 wherein the second end of the main body portion of the card assembly has a chevron shape that corresponds with the chevron-shaped openable seal of the sterile pouch such that when the chevron-shaped openable seal is opened, the second end and the finger hole of the main body portion extends outwardly from the sterile pouch.

12. The drill bit package assembly of claim 11 wherein the snap fit portion is connected to the main body portion along a fold, and wherein the snap fit portion is foldable between a non-deployed position and a deployed position.

13. The drill bit package assembly of claim 11 wherein the shield portion includes first and second flaps, wherein the main body portion includes first and second slots defined therein, and wherein the first and second flaps are received in the first and second slots when the shield portion is in the deployed position.

* * * * *